United States Patent [19]

Basile et al.

[11] Patent Number: 5,464,882

[45] Date of Patent: Nov. 7, 1995

[54] METHOD FOR INHIBITING THE DEGRADATION OF HYDROCHLOROFLUOROCARBONS UTILIZED AS FOAMING AGENTS IN THE PREPARATION OF FOAMED POLYURETHANES AND POLYISOCYANURATES

[75] Inventors: Giampiero Basile; Ezio Musso, both of Alessandria; Claudio Tonelli, Milan; Sauro Girolomoni, Alessandria, all of Italy

[73] Assignee: Ausimont S.p.A., Milan, Italy

[21] Appl. No.: 260,092

[22] Filed: Jun. 15, 1994

Related U.S. Application Data

[63] Continuation of Ser. No. 866,139, Apr. 9, 1992, abandoned.

[30] Foreign Application Priority Data

Apr. 11, 1991 [IT] Italy .................. MI91A0989
Jul. 5, 1991 [IT] Italy .................. MI91A1861

[51] Int. Cl.⁶ ............................................. C08J 9/14
[52] U.S. Cl. .................. 521/95; 521/98; 521/128; 521/131; 521/155; 521/170
[58] Field of Search .................. 521/98, 128, 131, 521/155, 170, 95

[56] References Cited

U.S. PATENT DOCUMENTS 3,085,116 4/1963 Kvalnes .
4,463,189 7/1984 Hoffmann et al. .
4,997,589 3/1991 Lund et al. .................. 521/98
5,035,833 7/1991 Ogawa et al. .................. 521/98
5,124,503 6/1992 Li et al. .................. 252/364
5,137,929 8/1992 Demmin et al. .................. 521/99

FOREIGN PATENT DOCUMENTS 0076471 4/1983 European Pat. Off. .
52-003006 1/1977 Japan .
63-075020 4/1988 Japan .
1128944 5/1989 Japan .
1128945 5/1989 Japan .
1-211538 8/1989 Japan .
1-211539 8/1989 Japan .
2279634 11/1990 Japan .
3031222 2/1991 Japan .
1009041 11/1965 United Kingdom .
1018809 2/1966 United Kingdom .
1149458 4/1969 United Kingdom .

*Primary Examiner*—James J. Seidleck
*Assistant Examiner*—John M. Cooney, Jr.
*Attorney, Agent, or Firm*—Bryan Cave

[57] ABSTRACT

The invention relates to a method for inhibiting the degradation by dehydrohalogenation of hydrochlorofluorocarbons, such as for example the mixture of 123 and 123a, used as foaming agents during the formation reaction of foamed polyurethanes or polyisocyanurates starting from polyols and polyisocyanates. Prior to the reaction starting, a little amount of a stabilizing substance selected from the group consisting of nitromethane, nitroethane and 1-nitropropane is added to the reaction medium.

7 Claims, No Drawings

METHOD FOR INHIBITING THE DEGRADATION OF HYDROCHLOROFLUOROCARBONS UTILIZED AS FOAMING AGENTS IN THE PREPARATION OF FOAMED POLYURETHANES AND POLYISOCYANURATES

This is a continuation of U.S. application Ser. No. 07/866,139 filed Apr. 9, 1992, now abandoned.

It is known that hydrochlorofluorocarbons, which are replacing the chlorofluorocarbons in their various applications, exhibit a lower chemical stability as compared with the latter, making them more subject to degradation in the presence of various substances and materials which they come in contact with during their various uses.

This problem arises in particular when the hydrochlorofluorocarbons are utilized as foaming agents in the preparation of foamed polyurethanes or polyisocyanurates. As is known, these products can be prepared by reacting polyalcohols with polyisocyanates in the presence of aminic and organometallic catalysts and of a foaming agent consisting of a hydrochlorofluorocarbon having a boiling temperature not higher than about 70° C.

When chlorofluorocarbons are utilized as foaming agents, a formulation based on polyol, catalysts and foaming agent is previously prepared. Such formulation is mixed with the polyisocyanate at the moment of carrying out the reaction. As it is usual to store the formulation even for several months, the chlorofluorocarbon tends to react with the organic compounds containing active hydrogen such as polyols and aminic catalysts.

Furthermore, the metals from the containers exert a catalytic action on the reaction between chlorofluorocarbons and organic compounds containing active hydrogen atoms. Thus a stabilizing agent capable of inhibiting the last-mentioned reaction is needed.

With the addition of such agent, the problems caused by the incompatibility between chlorofluorocarbons and polyols are also solved during the reaction between polyols and polyurethanes.

According to British patent No. 1,009,041, the reaction between chlorofluorocarbons, in particular $CFCl_3$, and polyols is inhibited by adding particular ethylenically unsaturated compounds such as alpha-methylstyrene.

According to British patent No. 1,018,809, the same reaction is inhibited by means of the same alpha-methylstyrene or other ehtylenically unsaturated compounds. The use of particular unsaturated hydrocarbons is described in British patent No. 1,149,458 and in U.S. Pat. No. 4,463,189. According to U.S. Pat. No. 3,085,116, the abovesaid reaction is inhibited by means of a mononitroalkane.

There are few documents which relate to the stabilization of hydrochlorofluorocarbons in the abovesaid formulations.

Among these documents, Japanese patent application 1-211538 describes a method for stabilizing hydrochlorofluorocarbons such as HCFC 123 by using acrylic or methacrylic esters containing at least a hydroxylic, ethereal or epoxy group.

Japanese patent application 1-211539 describes a method for stabilizing the same hydrochlorofluorocarbons by using one of the abovesaid esters and a hydrocarbon of formula:

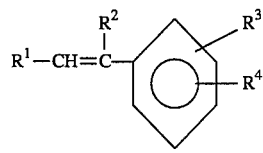

where $R^1$, $R^2$, $R^3$ and $R^4$ are hydrogen atoms or hydrocarbon groups containing 1 to 3 carbon atoms.

Applicants have now found that for several hydrochlorofluorocarbons, such as for example HCFC 123, it is not sufficient to add a stabilizer to the formulation, but it is necessary, above all, to stabilize them during the formation reaction of foamed polyurethane. During such reaction, several HCFC compounds decompose, giving rise to other degradation products, different from the ones which form during the storing of the HCFC-containing polyol.

These degradation products, as well as the ones which form during said storing, are often toxic.

While, for example, during the storing HCFC 123 ($CF_3$—$CHCl_2$) tends to decompose to the impurity HCFC 133a ($CH_2Cl$—$CF_3$), during the foamed polyurethane formation reaction, a dehydrofluorination reaction occurs, which leads to the formation of olefin CFC 1112a ($CF_2$=$CCl_2$).

The degradation reactions, which occur during the formation of foamed polyurethane, are thought to depend on the concomitant action of Lewis bases, which are present in the reaction medium, and on the temperature. The Lewis bases which are present in the reaction medium are polyalcohols and aminic catalysts.

As already mentioned, HCFC 123 leads to the formation of the olefin CFC 1112a.

Conversely, HCFC 123a (CHClF—$CF_2Cl$) leads to the formation of the olefin CFC 1113 (CClF=$CF_2$).

Both olefins are toxic.

Since HCFC 123—to be put on the market—which is a foaming agent of particular interest for the preparation of the abovesaid foamed products, can contain a certain amount of HCFC 123a—depending on the preparation process—the use of the mixture of HCFC 123 and HCFC 123a can give rise to the simultaneous formation of the abovesaid olefinic impurities.

Conversely, HCFC 141b ($CH_3$—$CCl_2F$) can lead to the formation of olefin HCFC 1131a ($CH_2$=CClF), which is toxic too.

Apart from the generation of generally toxic impurities, the abovesaid degradation reactions cause other drawbacks, which are due to the introduction of HCl and/or HF into the reaction medium and into the foamed products. In the first place these acids are corrosive and can damage the metallic and non-metallic materials of the structures which they come in contact with.

Furthermore, they tend to deactivate the basic catalysts, which play a leading role in controlling the foam generation rate so that it is in accordance with the polymerization rate.

In some cases, toxic olefins can form not by dehydronalogenation of the HCFC used as foaming agents, but instead from other HCFC which have formed due to other degradation reactions of the foaming HCFC. In particular, HCFC 123 can form radicals

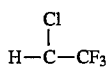

which, by coupling, can form HCFC 336 $CF_3$—CHCl—CHCl—$CF_3$, which is converted to toxic olefin HCFC 1326 $CF_3$—CH=CCl—$CF_3$ by dehydrochlorination. The last-cited type of degradation reaction gives rise, of course, to the same drawbacks as occur in the dehydrohalogenation reactions of the HCFC used as foaming agents.

As already mentioned herein, no method for inhibiting the abovesaid degradation reactions has been proposed so far.

Thus, it is an object of the present invention to provide a method for inhibiting such reactions by adding a little amount of a stabilizer to the reaction medium prior to the starting of the formation reaction of foamed polyurethane or polyisocyanurate, i.e. prior to the so-called "foaming".

Another object is to inhibit the formation of toxic olefins during foaming.

Still another object is to inhibit the formation of HCl and/or HF during foaming, thereby eliminating or reducing the drawbacks due to such formation.

These and still other objects are achieved by the method according to the present invention for inhibiting the degradation by dehydrohalogenation of hydrochlorofluorocarbons having two carbon atoms, on the first of which there is a chlorine or fluorine atom while on the second there is a hydrogen atom, the other atoms which are present on the two carbon atoms being indifferently H, Cl or F, with a total number of F atoms present in the molecule not higher than 4, and having a boiling temperature ranging from about $-15°$ C. to about 70° C., when said hydrochlorofluorocarbons are utilized as foaming agents during the formation reaction of foamed polyurethanes or polyisocyanurates starting from polyols and polyisocyanates and for inhibiting the dehydrohalogenation of hydrochlorofluorocarbons which form as degradation by-products of the abovesaid foaming agents during the aforesaid reaction.

This method is characterized in that a little amount of a stabilizer selected from the group consisting of nitromethane, nitroethane and 1-nitropropane is added to the reaction medium prior to the reaction starting.

The amount of added nitromethane generally ranges from 0.3 to 4% by weight calculated on the HCFC, the amount of added nitroethane generally ranges from 0.5 to 5% by weight and the amount of 1-nitropropane generally ranges from 0.5 to 5% by weight.

It is often preferred to use an amount of 0.5–1% by weight of nitromethane, 1–2% of nitroethane and 1–3% of 1-nitropropane.

The preferred stabilizing agent is nitromethane.

Among the hydrochlorofluorocarbons which are stabilized by the method according to the present invention there are to be cited, in particular, HCFC 123 ($CF_3$—$CHCl_2$), HCFC 141b ($CH_3$—$CCl_2F$), HCFC 123a ($CHCl$-$CClF_2$) and HCFC 141a ($CHCl_2$—$CH_2F$) and the mixtures of 123 and 123a and 141b and 141a.

The hydrochlorofluorocarbons which form as degradation by-products, as explained above, have generally 4 carbon atoms, wherein on one of two adjacent carbon atoms there is a Cl or F atom and on the other carbon atom there is a H atom, while the other atoms which are present on the two adjacent carbon atoms are indifferently H, Cl or F atoms.

In the cases in which the HCFC can react with the polyols and the amines contained in the polyol-based formulations—such cases being ascertainable by means of a storing test—it is convenient to mix the ingredients for the preparation of the foamed polymer (formulation based on polyol, polyisocyanate and HCFC) along with the stabilizer just before starting the foaming, or to mix the stabilizer-containing HCFC with the polyol-based formulation or with the polyisocyanate shortly before (i.e. within, for example, 24 hours) starting the foaming. The solution of the stabilizer in the HCFC can be stored for several months.

However, nitromethane, nitroethane and 1-nitropropane efficaciously inhibit the degradation of many of the HCFC defined above when the polyol-based formulations containing such HCFC are subjected to storing. That is the case of HCFC 123 and HCFC 141b. The amounts of stabilizers are the same as the ones utilized for the foaming.

An effective stabilization of several HCFC, for example HCFC 123 and HCFC 141b, is also obtained with particular unsaturated substances, which will be described below.

Conversely, in the case of HCFC 123a, none of the abovementioned classes of products is capable of efficaciously inhibiting its degradation in olefin 1113 ($CClF$=$CF_2$) during the polyol storing.

Instead of adding the hydrochlorofluorocarbons and nitromethane, nitroethane or 1-nitropropane before the foaming, it is therefore possible to add them, in various cases, to the polyol-based formulation prior to its storing.

It is also possible, in various cases, to add the HCFC stabilized with particular ethylenically unsaturated additives to the polyol-based formulation prior to its storing and then to add nitromethane, nitroethane or 1-nitropropane before starting the foaming.

The ethylenically unsaturated additives do not exert any stabilizing action during the foaming, as will be shown in comparative example No. 9.

Among the ethylenically unsaturated additives suited to stabilize several of the above-defined HCFC, in particular HCFC 123 and HCFC 141b, during the polyol storing, a first class which is an object of the present invention, consists of straight or branched polyalkenes containing at least a pair of conjugated ethylenic double bonds, having 4 to 8 carbon atoms in the straight part of the chain and optionally containing one or more substituent groups —$OCH_3$.

Other stabilizers, which are suitable for inhibiting the abovesaid reaction of several HCFC with the polyols during the formulation storing, are arylalkenes usually containing from 2 to 9 aliphatic carbon atoms and from 1 to 3 aromatic groups; said arylalkenes have at least an ethylenic double bond conjugated with one of the aromatic nuclei and optionally contain one or more -$OCH_3$ substituent groups on the aliphatic carbon atoms and/or in the aromatic groups; the aromatic groups are generally selected from the class consisting of phenyl, diphenyl, p-oxyphenyl phenyl and naphthyl.

Examples of suitable polyalkenes are: allocymene $CH_3$—CH=C($CH_3$)—CH=CH—CH=C($CH_3$)$_2$ 2,5-dimethyl-hexadiene 2,4, 1-methoxy-1,3-butadiene, butadiene and isoprene.

Examples of suitable arylalkenes are: the dimer of alpha-methylstyrene (a mixture of isomers 2,4-diphenyl-4-methyl-1-pentene and 2,4-diphenyl-4-methyl-2-pentene, the former being decidedly prevailing), anethol, m-diisopropenylbenzene, and 1,3,5-triisopropenylbenzene.

The polyalkene or arylalkene amount, expressed with respect to the hydrochlorofluorocarbon, generally ranges from 0.1 to 2.5% by weight and, preferably, from 0.5 to 1.5%.

The following examples are given for illustrative purposes and cannot be considered as a limitation of the scope of the present invention.

EXAMPLES 1–3

The polyol-based formulation was VORANOL XZ 00 88 011 produced by Dow Chemical, having a hydroxyl number of 400 and a water content equal to 2.4 parts for 100 of polyol. The HCFC was a mixture containing 88% by weight of 123 and 12% of 123a. The stabilizer and its amount are indicated in Table 1.

The polyisocyanate was TEDIMONT 31 produced by Enichem, having a number of isocyanate groups equal to 31% by weight and a mean functionality equal to 2.7.

The foaming was effected in a cylindrical cardboard vessel having a diameter of 15 cm and a height of 30 cm. 50 g of polyol formulation were mixed with 18 g of HCFC 123+123a until obtainment of a homogeneous solution. 80 g of polyisocyanate were then added in a few seconds and the mixture was poured into the vessel. During the forming of the foam, a maximum temperature ranging from 140° to 150° C., depending on the tests, was reached. On conclusion of the foaming, the whole was allowed to stand for 24 hours.

The foamy mass was then destroyed in a previously degassed vessel and the evolved gases were analyzed by means of gas chromatography.

The CFC 1113/HCFC 123+123a ratio and the CFC 1112a/HCFC 123+123a ratio were determined; they are reported in Table 1.

TABLE 1

| Test No. | Stabilizer % by wg. on HCFC 123 + 123a | CFC 1113 ppm on HCFC 123 + 123a | CFC 1112a ppm on HCFC 123 + 123a |
|---|---|---|---|
| 1 |  | 0 | 6300 | 514 |
| 2 | $CH_3NO_2$ | 0.5 | 73 | 27 |
| 3 | $CH_3NO_2$ | 1 | 21 | 15 |
| 3 bis | $C_2H_5NO_2$ | 1 | 2050 | 161 |

EXAMPLES 4–6

In these examples, the HCFC was composed of a mixture of 95.5% by weight of 123 and 4.5% of 123a.

It was operated in like manner as in examples 1–3.

The obtained results are reported in Table 2.

TABLE 2

| Test No. | Stabilizer % by wg. on HCFC 123 + 123a | CFC 1113 ppm on HCFC 123 + 123a | CFC 1112a ppm on HCFC 123 + 123a |
|---|---|---|---|
| 4 |  | 0 | 3,257 | 800 |
| 5 | $CH_3NO_2$ | 0.6 | 36 | 19 |
| 6 | $CH_3NO_2$ | 1 | 25 | 21 |

EXAMPLES 7–9

In these examples, the HCFC was 123 free from 123a.

It was operated in like manner as in examples 1–3.

Test No. 9 was carried out, as a comparative example, with an olefinic stabilizer i.e. alpha-methylstyrene.

The obtained results are reported in Table 3.

TABLE 3

| Test No. | Stabilizer % by wg. on HCFC 123 | | CFC 1113 ppm on HCFC 123 | CFC 1112a ppm on HCFC 123 |
|---|---|---|---|---|
| 7 |  | 0 | 0 | 1,065 |
| 8 | $CH_3NO_2$ | 1 | 0 | 22 |
| 9 | α-methylstyrene | 1 | 0 | 1,010 |

EXAMPLES 10–12

The polyol-based formulation contained polyols-polyethers with a hydroxyl number ranging from 400 to 500 and had a water content equal to 2.5 parts for 100 parts of polyols-polyethers.

The HCFC was a mixture containing 95.5% by weight of 123 and 4.5% of 123a.

The polyisocyanate was the same as in examples 1–3.

It was operated in like manner as in examples 1 to 3, introducing 50 g of polyol-based formulation, 16.5 g of HCFC 123+123a and 73.5 g of polyisocyanate.

The obtained results are reported in Table 4.

TABLE 4

| Test No. | Stabilizer % by weight on HCFC 123 + 123a | | CFC 1113 ppm on HCFC 123 + 123a | CFC 1112a ppm on HCFC 123 + 123a |
|---|---|---|---|---|
| 10 |  | 0 | 77 | 0 |
| 11 | $CH_3NO_2$ | 0.3 | 29 | 0 |
| 12 | $CH_3NO_2$ | 1 | 24 | 0 |
| 12 bis | $C_2H_5NO_2$ | 1.5 | 39 | 0 |
| 12 ter | $C_3H_7NO_2$ | 2.5 | 32 | 0 |

EXAMPLES 13–14

It was operated in like manner as in examples 10–12, but instead of effecting the foaming in a non-externally heated vessel, it was effected in the same vessel used in examples 1–3, placed in an oven thermoregulated at 140° C. On conclusion of the reaction, after about 30 minutes, the foamy material was taken out from the oven and was allowed to stand for 24 hours. The obtained results are reported in Table 5.

TABLE 5

| Test No. | Stabilizer % by wg. on HCFC 123 + 123a | | CFC 1113 ppm on HCFC 123 + 123a | CFC 1112a ppm on HCFC 123 + 123a |
|---|---|---|---|---|
| 13 |  | 0 | 778 | 123 |
| 14 | $CH_3NO_2$ | 1 | 35 | 24 |

EXAMPLES 15-26

These examples refer to an accelerated storing test of a polyether-polyol-based formulation for the preparation of polyurethanes, containing HCFC 123, in the presence or absence of various stabilizers.

The formulation used in an amount of 25 g, was the composition BVH-D040116 produced by Bayer, containing a polyether-polyol with a hydroxyl number of 490 and a little amount of water and of an organometallic catalyst.

The stabilizer was used in an amount of 0.4% by weight referred to HCFC 123.

The test was conducted at 50° C. for 21 days.

The amounts of the various agents are indicated in Table 6. The stabilization effectiveness was evaluated by measuring, on conclusion of the test, the number of ppm of toxic impurity HCFC 133a with respect to HCFC 123 by means of gas chromatography.

Tests 15-18, conducted under identical conditions, show the efficaciousness of two stabilizers conforming to the invention (tests 16 and 17) and the negligible stabilizing effect of an ethylenically unsaturated substance not conforming to the present invention (test 18).

In tests 19-21 an aminic catalyst (triethylamine) was present, which enhanced the tendency to degradation.

In tests 22-24 a previously degreased sheet-iron was present, which exhibited a surface of 0.22 cm$^2$ per cm$^3$ of mixture.

In tests 25-26 the triethylamine and the sheet-iron were contemporaneously present. The test without stabilizer was not carried out, but it is evident that it would have given worse results than the ones of test 22.

EXAMPLES 27-29

In tests 27-29 the influence of increasing nitroethane amounts is illustrated.

The formulation (25 g) was the same as in examples 15-26.

The amounts of the various agents and the obtained results are reported in Table 7. The HCFC 133a amounts were determined by gas chromatography.

No test without stabilizer was carried out, but it is evident that it would have given worse results than the ones of test 22 of Table 6.

EXAMPLES 30-33

These tests were conducted at high temperature (120° C.) for a time of 24 hours.

Instead of using a formulation based on polyols for polyurethanes, the diglyme $$CH_3-(OCH_2-CH_2)_2-OCH_3$$

was used as an organic substance containing reactive hydrogen atoms.

The HCFC 133a amount, determined on conclusion of the tests by means of NMR, is indicated in ppm referred to HCFC 123.

The complete data of the tests are reported in Table 8 along with the results.

In tests 30-31, iron filings was added; in tests 32-33, a catalyst for the formation reaction of polyurethanes (consisting of dibutyltin dilaurate) was added.

TABLE 6

| Test | Formulation | HCFC 123 | Triethyl-amine | Sheet-iron | Stabilizer (0,4% by weight referred to HCFC 123) | ppm HCFC 133a |
|---|---|---|---|---|---|---|
| 15 | 100 | 35 | | | without | 706 |
| 16 | 100 | 35 | | | allocymene | 125 |
| 17 | 100 | 35 | | | nitroethane | 70 |
| 18 | 100 | 35 | | | diisobutylene | 600 |
| 19 | 100 | 35 | 2 | | without | 1050 |
| 20 | 100 | 35 | 2 | | allocymene | 205 |
| 21 | 100 | 35 | 2 | | nitroethane | 145 |
| 22 | 100 | 35 | | present | without | 2735 |
| 23 | 100 | 35 | | present | allocymene | 435 |
| 24 | 100 | 35 | | present | nitroethane | 290 |
| 25 | 100 | 35 | 2 | present | allocymene | 460 |
| 26 | 100 | 35 | 2 | present | nitroethane | 315 |

TABLE 7

| Test | Formulation | HCFC 123 | Triethyl-amine | Sheet-iron | Stabilizer (% by weight referred to to HCFC 123) | ppm HCFC 133a |
|---|---|---|---|---|---|---|
| 27 | 100 | 35 | 2 | present | nitroethane 0.34 | 280 |
| 28 | 100 | 35 | 2 | present | nitroethane 0.69 | 150 |
| 29 | 100 | 35 | 2 | present | nitroethane 1.01 | 95 |

TABLE 8

| Test | Diglyme | HCFC 123 | Iron filings | Organometal-lic catalyst | Stabilizer | ppm HCFC 133a |
|---|---|---|---|---|---|---|
| 30 | 217 mg | 650 mg | 25 mg | | without allocymene | 3234 |
| 31 | 217 mg | 650 mg | 25 mg | | 10 mg | 411 |
| 32 | 217 mg | 650 mg | | 2,5 mg | without allocymene | 2328 |
| 33 | 217 mg | 650 mg | | 2,5 mg | 10 mg | <10 (analytical limit) |

EXAMPLES 34–42

It was operated in like manner as in examples 15–26, utilizing the Bayer composition BVH-D040116, but using HCFC 141b instead of HCFC 123, in an amount of 34.56 parts by weight for 100 parts of polyol. Furthermore, the tests were conducted for longer stretches of time of 31, 53 and 85 days, respectively. The utilized stabilizers were nitromethane and nitroethane.

The stabilizer amounts and the obtained results are reported in Table 9.

From an examination of the Table it can be noticed that the two stabilizers inhibit the degradation of HCFC 141b to HCFC 151a, which is toxic.

TABLE 9

| TEST NO. | AGEING TIME (days) | STABILIZER | % by weight on HCFC 141 b | HCFC 151a: ppm by weight on HCFC 141b |
|---|---|---|---|---|
| 34 | 31 | | 0 | 145 |
| 35 | 31 | $CH_3NO_2$ | 0.409 | 13 |
| 36 | 31 | $C_2H_5NO_2$ | 0.409 | 20 |
| 37 | 53 | | 0 | 169 |
| 38 | 53 | $CH_3NO_2$ | 0.319 | 23 |
| 39 | 53 | $C_2H_5NO_2$ | 0.409 | 32 |
| 40 | 85 | | 0 | 207 |
| 41 | 85 | $CH_3NO_2$ | 0,319 | 46 |
| 42 | 85 | $C_2H_5NO_2$ | 0,409 | 64 |

EXAMPLES 43–46

It was operated in like manner as in examples 15–26, utilizing the Bayer composition BVH-D040116, using 35 parts by weight of HCFC 123 for 100 parts of polyol.

The utilized stabilizers, their amounts, the duration of the test and the obtained results are reported in Table 10.

TABLE 10

| TEST NO. | DURATION OF AGEING (days) | STABILIZER | % by weight on HCFC 123 | HCFC 133a: ppm by weight on HCFC 123 |
|---|---|---|---|---|
| 43 | 40 | | 0 | 1790 |
| 44 | 40 | $CH_3NO_2$ | 1.05 | 50 |
| 45 | 40 | $C_2H_5NO_2$ | 1.28 | 60 |
| 46 | 40 | $C_3H_7NO_2$ | 1.46 | 90 |

We claim:

1. A process for inhibiting dehydrohalogenation of hydrochlorofluorocarbons in a reaction medium consisting essentially of said hydrochlorofluorocarbons mixed with polyols and polyisocyanates for use in a foaming reaction to produce foamed polyurethanes or polyisocyanurates, said process comprising adding a dehydrohalogenation inhibiting agent to said reaction medium up to twenty-four hours before starting the foaming reaction to prevent said hydrochlorofluorocarbons from undergoing dehydrohalogenation in said reaction medium, wherein said hydrochlorofluorocarbons have two carbon atoms, the first of which is bound to a chlorine or fluorine atom, the second of which is bound to a hydrogen atom, while the remaining atoms bound to the two carbon atoms are selected from the group consisting of H, Cl and F, with the proviso that the total number of F atoms in the hydrochlorofluorocarbons is not higher than 4, and said hydrochlorofluorocarbons have a boiling temperature of from about −15° C. to about 70° C. and wherein said dehydrohalogenation inhibiting agent is selected from the group consisting of nitromethane, nitroethane and 1-nitropropane.

2. The process of claim 1, wherein the dehydrohalogenation inhibiting agent is nitromethane.

3. The process of claim 2, wherein the amount of nitromethane added to the reaction medium is from 0.3 to 4% by weight of the hydrochlorofluorocarbons in the reaction medium.

4. The process of claim 1, wherein the amount of nitroethane or 1-nitropropane added to the reaction medium is from 0.5 to 5% by weight of the hydrochlorofluorocarbons in the reaction medium.

5. The process of claim 1, wherein the dehydrohalogenation inhibiting agent is introduced into the reaction medium contemporaneously with the commencement of the foaming reaction.

6. The process of claim 1, wherein the hydrochlorofluorocarbon is selected from the group consisting of: 1,1-dichloro-2,2,2-trifluoroethane, 1,1-dichloro-1-fluoroethane, 1,2-dichloro-1,2,2-trifluoroethane, 1,1-dichloro-2-fluoroethane; mixtures of 1,1-dichloro-2,2,2-trifluoroethane and 1,2-dichloro-1,2,2-trifluoroethane; and mixtures of 1,1-dichloro-2-fluoroethane and 1,1-dichloro-1-fluoroethane.

7. The process of claim 1, wherein the hydrochlorofluorocarbon is selected from the group consisting of: 1,1-dichloro-2,2,2-trifluoroethane, 1,1-dichloro-1-fluoroethane, 1,2-dichloro-1,2,2-trifluoroethane, 1,1-dichloro-2-fluoroethane; mixtures of 1,1-dichloro-2,2,2-trifluoroethane and 1,2-dichloro-1,2,2-trifluoroethane; and mixtures of 1,1-dichloro-2-fluoroethane and 1,1-dichloro-1-fluoroethane.

* * * * *